(12) United States Patent
Bae et al.

(10) Patent No.: US 9,594,892 B2
(45) Date of Patent: Mar. 14, 2017

(54) USER AUTHENTICATION METHOD AND APPARATUS BASED ON ELECTROCARDIOGRAM (ECG) SIGNAL

(71) Applicants: Samsung Electronics Co., Ltd., Suwon-si (KR); Korea Advanced Institute of Science and Technology, Daejeon (KR)

(72) Inventors: Chisung Bae, Yongin-si (KR); Sang Joon Kim, Hwaseong-si (KR); Jin Woo Shin, Daejeon (KR)

(73) Assignees: Samsung Electronics Co., Ltd., Suwon-si (KR); Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 14/717,475

(22) Filed: May 20, 2015

(65) Prior Publication Data
US 2016/0063231 A1 Mar. 3, 2016

(30) Foreign Application Priority Data

Aug. 26, 2014 (KR) ........................ 10-2014-0111611

(51) Int. Cl.
*G06F 21/32* (2013.01)
*A61B 5/00* (2006.01)
(Continued)

(52) U.S. Cl.
CPC .......... *G06F 21/32* (2013.01); *A61B 5/04525* (2013.01); *A61B 5/117* (2013.01); *A61B 5/725* (2013.01); *A61B 5/7246* (2013.01); *A61B 5/7264* (2013.01); *G07C 9/00158* (2013.01); *H04L 9/3231* (2013.01); *H04L 29/06809* (2013.01)

(58) Field of Classification Search
CPC ....................................................... G06F 21/32
USPC ........................................................ 340/5.82
See application file for complete search history.

(56) References Cited

U.S. PATENT DOCUMENTS 8,189,703 B2   5/2012   Feher
8,301,236 B2   10/2012  Baumann et al.
(Continued)

FOREIGN PATENT DOCUMENTS

EP   2 722 001 A1   4/2014
JP   4257538 B2    4/2009
(Continued)

OTHER PUBLICATIONS

S. Pal, et al., "Increasing the accuracy of ECG based biometric analysis by data modelling," *Measurement*, vol. 45, No. 7, 2012, pp. 1927-1932.
(Continued)

*Primary Examiner* — Kevin Kim
(74) *Attorney, Agent, or Firm* — NSIP Law

(57) ABSTRACT

An authentication apparatus includes an electrocardiogram (ECG) signal receiver configured to receive a target ECG signal, and a preprocessor configured to filter the target ECG signal. The apparatus further includes an authenticator configured to process the filtered target ECG signal based on a pattern of a reference ECG signal, and determine whether the target ECG signal corresponds to the reference ECG signal based on the processing.

21 Claims, 15 Drawing Sheets

(51) Int. Cl.
*A61B 5/0452* (2006.01)
*A61B 5/117* (2016.01)
*G07C 9/00* (2006.01)
*H04L 9/32* (2006.01)
*H04L 29/06* (2006.01)

(56) References Cited

U.S. PATENT DOCUMENTS

| | | |
|---|---|---|
| 8,607,319 B2 | 12/2013 | Peirce |
| 2005/0240778 A1 | 10/2005 | Saito |
| 2006/0136744 A1 | 6/2006 | Lange |
| 2013/0173926 A1 | 7/2013 | Morese et al. |
| 2014/0165184 A1* | 6/2014 | Lange .................... G06F 21/32 726/19 |
| 2015/0373019 A1* | 12/2015 | El Saddik ........... H04L 63/0861 340/5.52 |

FOREIGN PATENT DOCUMENTS

| | | |
|---|---|---|
| JP | 2012-210235 A | 11/2012 |
| JP | 2013-150806 A | 8/2013 |
| KR | 10-0685784 B1 | 2/2007 |
| KR | 10-1002020 B1 | 12/2010 |
| KR | 10-1192932 B1 | 10/2012 |
| KR | 10-2013-0140439 A | 12/2013 |
| WO | WO 2006/048701 A2 | 5/2006 |
| WO | WO 2012/151680 A1 | 11/2012 |

OTHER PUBLICATIONS

S. Venugopalan, et al., "Analysis of Low-Dimensional Radio-Frequency Impedance-Based Cardio-Synchronous Waveforms for Biometric Authentication," *IEEE Transactions on Biomedical Engineering*, vol. 61, No. 8, Aug. 2014, pp. 2324-2335.

M. Yang, et al., "Normalizing Electrocardiograms of Both Healthy Persons and Cardiovascular Disease Patients for Biometric Authentication," *PLOS One, Open Access*, vol. 8, Issue 8, Aug. 2013, pp. 1-8.

Extended European Search Report issued on Jan. 20, 2016, in counterpart of European Application No. 15170249.5 (9 pages, in English).

* cited by examiner

USER AUTHENTICATION METHOD AND APPARATUS BASED ON ELECTROCARDIOGRAM (ECG) SIGNAL

CROSS-REFERENCE TO RELATED APPLICATION

This application claims the benefit under 35 USC 119(a) of Korean Patent Application No. 10-2014-0111611, filed on Aug. 26, 2014, in the Korean Intellectual Property Office, the entire disclosure of which is incorporated herein by reference for all purposes.

BACKGROUND

1. Field

The following description relates to a user authentication method and a user authentication apparatus based on an electrocardiogram (ECG) signal.

2. Description of Related Art

Biometric technology may refer to technology for extracting a signal or data associated with a body of a user and comparing a result of the extracting to pre-stored data, thereby authenticating the user as a registered user through identification. A personal biosignal may not be stolen or lost due to an intrinsic uniqueness. Thus, the biometric technology based on the personal biosignal may be robust against forgery or falsification.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided an authentication apparatus including an electrocardiogram (ECG) signal receiver configured to receive a target ECG signal, a preprocessor configured to filter the target ECG signal, and an authenticator configured to process the filtered target ECG signal based on a pattern of a reference ECG signal, and determine whether the target ECG signal corresponds to the reference ECG signal based on the processing.

The preprocessor may be configured to align the target ECG signal based on an R peak of the target ECG signal, and normalize the target ECG signal based on a time interval between consecutive R peaks of the target ECG signal.

The normalizer may be configured to normalize an amplitude of the target ECG signal based on a predetermined voltage level.

The authenticator may be configured to determine a difference between the filtered target ECG signal and the reference ECG signal, and eliminate, from the difference, the pattern of the reference ECG signal.

The authenticator may be configured to extract an ECG vector based on an ECG waveform of the filtered target ECG signal, and extract an error matrix indicating the difference between the filtered target ECG signal and the reference ECG signal based on a difference between an average vector indicating an average of ECG waveforms of the reference ECG signal and the ECG vector.

The authenticator may be configured to eliminate, from the error matrix, dominant error matrix components of the reference ECG signal, the dominant error matrix components indicating the pattern.

The authenticator may be configured to determine a norm of the error matrix from which the dominant error matrix components are eliminated, and determine whether the target ECG signal corresponds to the reference ECG signal based on the norm.

The authenticator may be configured to authenticate the target ECG signal as corresponding to the reference ECG signal in response to the norm being less than or equal to a predetermined norm.

In response to reference ECG signals being acquired, the authenticator may be configured to extract the norm for each of the reference ECG signals, and authenticate a reference ECG signal having a smallest norm among the reference ECG signals as corresponding to the target ECG signal.

In another general aspect, there is provided a registration apparatus including an electrocardiogram (ECG) signal receiver configured to receive an ECG signal, and a preprocessor configured to filter the ECG signal. The apparatus further includes a register configured to extract a pattern from the filtered ECG signal, and register information of the ECG signal, the information including the pattern.

The preprocessor may be configured to align the ECG signal based on an R peak of the ECG signal, and normalize the ECG signal based on a time interval between consecutive R peaks of the ECG signal.

The register may be configured to store the pattern.

The register may be configured to determine a difference between the filtered ECG signal and an average of the filtered ECG signal.

The register may be configured to extract ECG vectors based on ECG waveforms of the filtered ECG signal, and extract an average vector indicating the average of the filtered ECG signal by determining an average of the ECG vectors.

The register may be configured to extract an error matrix based on a difference between the average vector and each of the ECG vectors, and extract a dominant error matrix indicating dominant error components from the error matrix based on a singular value decomposition (SVD) scheme.

A rank of the dominant error matrix may be lower than a rank of the error matrix.

In still another general aspect, there is provided an authentication apparatus including an electrocardiogram (ECG) signal receiver configured to receive a first ECG signal and a second ECG signal, and a preprocessor configured to filter the first ECG signal and the second ECG signal. The apparatus further includes a register configured to extract a pattern from the filtered first ECG signal, and register information of the first ECG signal, the information including the pattern, and an authenticator configured to process the filtered second ECG signal based on the pattern of the filtered first ECG signal, and determine whether the second ECG signal corresponds to the first ECG signal based on the processing.

The preprocessor may be configured to align the first ECG signal and the second ECG signal based on an R peak of the first ECG signal and an R peak of the second ECG signal, respectively, and normalize the first ECG signal and second ECG signal based on time intervals between consecutive R peaks of the first ECG signal and time intervals between consecutive R peaks of the second ECG signal, respectively.

The register may be configured to extract first ECG vectors based ECG waveforms of the filtered first ECG signal, and extract an average vector indicating an average of the filtered first ECG signal by determining an average of the first ECG vectors.

The register may be configured to extract a first error matrix based on a difference between the average vector and each of the first ECG vectors, and extract a dominant error matrix indicating dominant error components from the first error matrix based on a singular value decomposition (SVD) scheme.

The authenticator may be configured to extract a second ECG vector based on a second ECG waveform of the filtered second ECG signal, extract a second error matrix indicating a difference between the filtered second ECG signal and the filtered first ECG signal based on a difference between the average vector and the second ECG vector, and eliminating, from the second error matrix, dominant error matrix components of the filtered first ECG signal, the dominant error matrix components indicating the pattern.

The authenticator may be configured to determine a norm of the second error matrix from which the dominant error matrix components are eliminated, and determine whether the second ECG signal corresponds to the first ECG signal based on the norm.

In yet another general aspect, there is provided a method including filtering a first ECG signal, and determining whether the first ECG signal corresponds to a second ECG signal based on the filtered first ECG signal, the second ECG signal, and a pattern of the second ECG signal.

The determining may include determining a difference between the filtered first ECG signal and the second ECG signal, eliminating, from the difference, the pattern of the second ECG signal, and determining whether the first ECG signal corresponds to the second ECG signal based on the difference from which the pattern of the second ECG signal is eliminated.

The method may further include filtering the second ECG signal, extracting a pattern from the filtered second ECG signal, and registering the extracted pattern as the pattern of the second ECG signal.

The extracting may include determining a difference between the filtered second ECG signal and an average of the filtered second ECG signal, and extracting, from the difference, the pattern of the filtered second ECG signal.

Other features and aspects will be apparent from the following detailed description, the drawings, and the claims.

Figure 1:
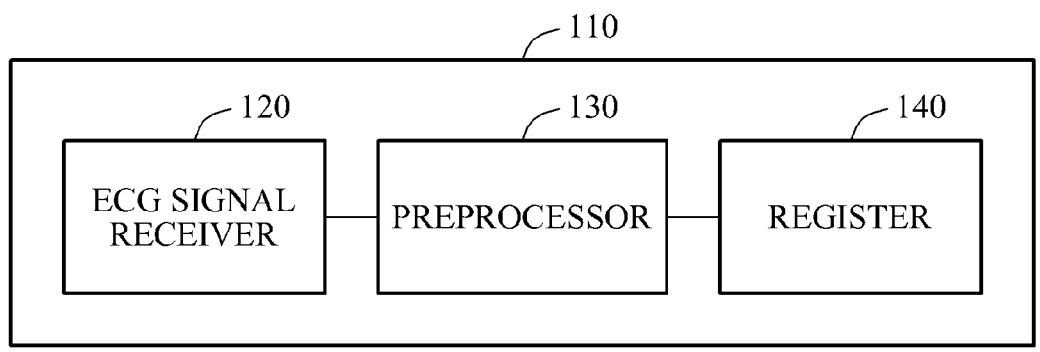
FIG. 1 is a block diagram illustrating an example of a registration apparatus.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Figure 2:
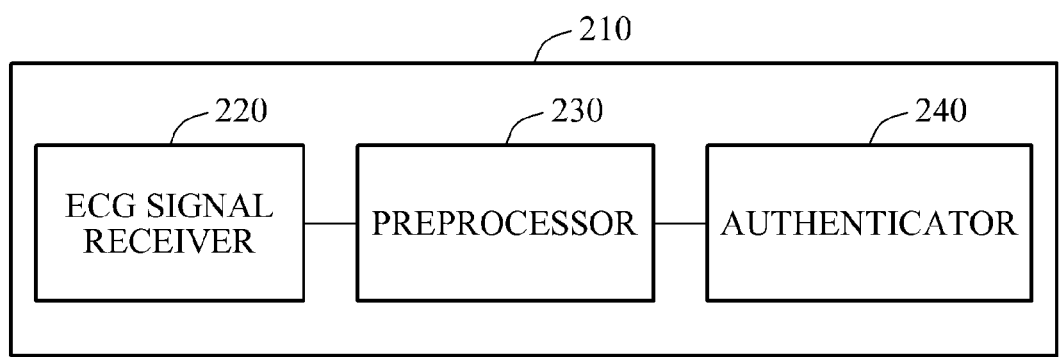
FIG. 2 is a block diagram illustrating an example of an authentication apparatus.

FIG. 1 is a block diagram illustrating an example of a registration apparatus 110. Referring to FIG. 1, the registration apparatus 110 includes an electrocardiogram (ECG) signal receiver 120, a preprocessor 130, and a register 140. The registration apparatus 110 registers an ECG signal of a user. An authentication apparatus 210 of FIG. 2 compares ECG information acquired to perform an authentication and ECG information registered in the registration apparatus 110 in advance, thereby authenticating whether a user of an acquired ECG signal corresponds to a user of a pre-registered ECG signal. In an example, although the registration apparatus 110 is described as being separate from the authentication apparatus 210 of FIG. 2, the registration apparatus 110 and the authentication apparatus 210 may be configured in a single apparatus or to be separate from one another.

The ECG signal receiver 120 receives the ECG signal of the user, using an ECG sensor. The ECG sensor may include, for example, a plurality of electrodes, an analog front-end (AFE), and/or a digital filter. The electrodes may sense the ECG signal of the user through contact with, for example, finger skin of the user. The AFE may amplify the ECG signal sensed by the electrodes, and convert the amplified ECG signal into a digital signal. Among the amplified ECG signal, the digital filter may allow passing of an ECG frequency band, and eliminate other bands. Through this, a signal-to-noise ratio (SNR) of the ECG signal may be improved.

The preprocessor 130 processes the ECG signal to have a form appropriate for a user authentication. The ECG signal may have a variable time period and a variable intensity. For example, in an ECG signal of an identical user, a time period and an intensity may vary based on a respiration state of the user. Also, since the ECG signal is acquired through a sampling in the ECG sensor, a peak of the ECG signal acquired in the ECG sensor may be different from a peak of an actual ECG signal.

Although not shown in FIG. 1, the preprocessor 130 may include an aligner, a normalizer, and an eliminator. The aligner may align the ECG signal based on an R peak. A P wave, a QRS wave, a T wave, and a U wave may appear repetitively in the ECG signal, and the R peak of the QRS wave may have a greatest intensity. Thus, the aligner may align the ECG signal based on the R peak. In this example, the aligner may set an interval between consecutive R peaks as one time period, and align the ECG time period based on the set time period. Through this, the ECG signal may be aligned to be a plurality of ECG waveforms having the time period set based on the interval between the consecutive R peaks.

The normalizer may normalize the ECG signal based on the time period. In an example, the normalizer may set a length of the ECG signal as an equalized value. For example, when an RR-interval of a first ECG signal is 800 microseconds (μs), and when an RR-interval of a second ECG signal is 750 μs, the normalizer may set the RR-interval of each of the first and second ECG signals to 800 μs to normalize the first ECG signal and the second ECG signal. In this example, when the ECG signal is a discrete signal, the normalizer may normalize the ECG signal based on an interpolation scheme. In another example, the normalizer may normalize an amplitude of the ECG signal based on a predetermined voltage level. For example, the normalizer may set a maximum amplitude level of the first ECG signal and the second ECG signal as one millivolt (mV), and normalize the first ECG signal and the second ECG signal based on the set maximum amplitude level.

The eliminator may eliminate a component having a relatively low correlation from at least one component of the normalized ECG signal. For example, the eliminator may determine a correlation between components of the normalized ECG signal, and eliminate a component having a correlation lower than or equal to a predetermined threshold correlation, from the normalized ECG signal. The eliminator may determine the correlation between the components of the ECG signal based on, for example, a cosine similarity, a Pearson correlation, and a normalized root mean square error. When the eliminator eliminates the component having a low correlation from the at least one component from the normalized ECG signal, a number of operations may be reduced in the register 140, and a time for registering the ECG information of the user may also be reduced.

The register 140 extracts dominant error components and an average value of the filtered or processed ECG signal. When a plurality of filtered ECG signals is provided for a single user, the register 140 may extract the dominant error components and an average value of the filtered ECG signals.

The ECG signal filtered in the preprocessor 130 may include a predetermined variation, and the variation may reflect unique characteristics of the user. The predetermined variation may be expressed by a predetermined pattern, and the predetermined pattern may indicate the dominant error components of the filtered ECG signal. The register 140 may extract the average value of the filtered ECG signal in advance of extracting the dominant error components. The register 140 may extract a plurality of ECG vectors based on a plurality of ECG waveforms in the filtered ECG signal, and extract an average vector indicating the average value of the filtered ECG signal by determining an average of the ECG vectors. For example, when the filtered ECG signal includes a first ECG waveform indicating an ECG waveform between a first R peak and a second R peak and a second ECG waveform indicating an ECG waveform between the second R peak and a third R peak, the register 140 may extract the first ECG vector based on the first ECG waveform, and extract the second ECG vector based on the second ECG waveform. In this example, the first ECG vector may include an amplitude, for example, a voltage value of the first ECG waveform as an element, and the second ECG vector may include an amplitude of the second ECG waveform as an element. The register 140 may determine an average value of the first ECG vector and the second ECG vector, and determine an average vector including the average value of the first ECG vector and the second ECG vector as an element.

The register 140 may extract an error matrix based on a difference between the average vector and the at least one ECG vector, and extract a dominant error matrix indicating the dominant error components from the error matrix based on a k-rank approximation scheme. In an example, the register 140 may extract the dominant error matrix from the error matrix based on a singular value decomposition (SVD) scheme. As shown below, noise of the filtered ECG signal may be defined as a distance between the filtered ECG signal and the average value of the filtered ECG signal, using Equation 1.

$$N(i,j) = \text{average}_i - \text{signal}_i(j) \quad \text{[Equation 1]}$$

In Equation 1, $N(i,j)$ denotes noise occurring in a $j^{th}$ ECG waveform in a filtered ECG signal of an $i^{th}$ user, $\text{average}_i$ denotes an average value of the filtered ECG signal of the $i^{th}$ user, and $\text{signal}_i(j)$ denotes a value of the $j^{th}$ ECG waveform in the filtered ECG signal of the $i^{th}$ user. The register 140 may extract a plurality of ECG vectors based on a plurality of ECG waveforms in the filtered ECG signal of the $i^{th}$ user, and subtract an average vector of the filtered ECG signal from the ECG vectors, thereby generating an error matrix indicating noise of the filtered ECG signal. In an example, the register 140 may generate the error matrix, using Equation 2.

$$E_i = X_i - \overline{X}_i \quad \text{[Equation 2]}$$

In Equation 2, $E_i$ denotes an error matrix of the filtered ECG signal of the $i^{th}$ user, $X_i$ denotes an ECG matrix including the plurality of ECG vectors, and $\overline{X}_i$ denotes an average matrix including the average vector. Also, the error matrix may be approximated as shown in Equation 3.

$$E_i = X_i - \overline{X}_i \approx A_i B_i \quad \text{[Equation 3]}$$

In Equation 3, $A_i$ denotes a weight matrix of the filtered ECG signal of the $i^{th}$ user, and $B_i$ denotes a dominant error matrix of the filtered ECG signal of the $i^{th}$ user. The register 140 may decompose the error matrix $E_i$ into the weight matrix $A_i$ and the dominant error matrix $B_i$ based on an SVD scheme or a low rank approximation scheme. In this example, the dominant error matrix $B_i$ may indicate a pattern of the ECG signal based on unique characteristics of the $i^{th}$ user. Also, since the dominant error matrix $B_i$ is extracted by dividing the error matrix $E_i$, a rank of the dominant error matrix $B_i$ may be lower than a rank of the error matrix $E_i$.

The register 140 may store extracted information of the ECG signal including, for example, the average vector, the error matrix, and the dominant error matrix. The register 140 may also transmit the ECG information to the authentication apparatus 210 of FIG. 2 through a communication interface.

When a plurality of users uses the registration apparatus 110, the register 140 may store an average vector, an error matrix, and a dominant error matrix that correspond to each of the respective users.

FIG. 2 is a block diagram illustrating an example of the authentication apparatus 210. Referring to FIG. 2, the authentication apparatus 210 includes an ECG signal receiver 220, a preprocessor 230, and an authenticator 240. The authentication apparatus 210 authenticates whether a user is a pre-registered user based on an ECG signal of the user. The authentication apparatus 210 may compare ECG information of the pre-registered user stored in the registration apparatus 110 of FIG. 1 and ECG information acquired from the user, and authenticate whether the user corresponding to the acquired ECG information matches the pre-registered user. As described above, although the authentication apparatus 210 is described as being separate from the registration apparatus 110 of FIG. 1, the authentication apparatus 210 and the registration apparatus 110 may be configured in a single apparatus or to be separate from one another. As described with reference to FIG. 11, when the registration apparatus 110 and the authentication apparatus 210 are configured in a single apparatus, an ECG signal receiver 1120 and a preprocessor 1130 may be used for both registration and authentication.

The ECG signal receiver 220 receives a target ECG signal indicating the ECG signal of the user, using an ECG sensor, and performs an identical operation to the operation of the ECG receiver 120 of FIG. 1. The preprocessor 230 filters and processes the target ECG signal to have a form appropriate for the authentication, and performs an identical operation to the operation of the preprocessor 130 of FIG. 1.

The authenticator 240 eliminates dominant error components and an average value of a reference ECG signal from the filtered target ECG signal, and determines whether the target ECG signal corresponds to the reference ECG signal. The reference signal is a pre-registered ECG signal of a user, and a plurality of reference ECG signals may be used for a plurality of users, respectively. In an example, the authenticator 240 may store information of the dominant error components and the average value of the reference ECG signal in advance. Also, the authenticator 240 may receive the information of the dominant error components and the average value of the pre-registered ECG signal from an external source, for example, the registration apparatus 110 of FIG. 1.

The authenticator 240 may extract an ECG vector based on an ECG waveform of the filtered target ECG signal. In this example, the authenticator 240 may generate the ECG vector including an amplitude, for example, a voltage value of the ECG waveform, as an element. Also, the authenticator 240 may extract an error matrix based on a difference between an average vector indicating the average value of the reference ECG signal and a plurality of ECG vectors. The authenticator 240 may eliminate dominant error matrix components indicating the dominant error components of the reference ECG signal from the error matrix, and determine a norm of the error matrix from which the dominant error matrix components are eliminated. In an example, the authenticator 240 may determine the norm, using Equation 4.

$$L_i = \|(y-\bar{x}_i) - \sum_{j=1}^{k}(y \cdot B_{ij}^T \cdot y)\| \quad \text{[Equation 4]}$$

In Equation 4, $L_i$ denotes a norm of an error matrix from which dominant error matrix components are eliminated, of an $i^{th}$ user, y denotes each of ECG vectors, $\bar{x}_i$ denotes an average vector of a reference ECG signal, and $B_{ij}$ denotes a $j^{th}$ row of a dominant error matrix. $\| \ \|$ denotes a norm indicating a length of a vector. In this example, the norm may indicate, for example, a Euclidean norm, an L1 norm, and/or a P norm. For example, when a target ECG signal of a user attempting to be authenticated includes a first ECG waveform and a second ECG waveform, the authenticator 240 may generate a first ECG vector and a second ECG vector based on the first ECG waveform and the second ECG waveform, and generate an error matrix $y-\bar{x}_i$ by subtracting the average vector of the reference ECG signal from the first ECG vector and the second ECG vector.

The authenticator 240 may determine whether the ECG signal corresponds to the pre-registered ECG signal based on the determined norm. In an example, the authenticator 240 may compare a norm of the error matrix and the norm of the error matrix from which the dominant error matrix components are eliminated, to determine whether the ECG signal corresponds to the pre-registered ECG signal. The authenticator 240 may determine the norm of the error matrix, using Equation 5, and determine the norm of the error matrix from which the dominant error matrix components are eliminated.

$$M_i \times \|(y-\bar{x}_i)\| \quad \text{[Equation 5]}$$

In Equation 5, $M_i$ denotes a norm of an error matrix of the $i^{th}$ user, y denotes each of the ECG vectors, and $\bar{x}_i$ denotes the average vector of the reference ECG signal. The dominant error matrix may indicate a pattern of the ECG signal based on unique characteristics of the pre-registered user. In this example, the eliminating of the dominant error matrix components from the error matrix may correspond to eliminating the unique characteristics of the pre-registered user from the target ECG waveform. When the user attempting authentication matches the pre-registered user, the eliminating of the dominant error matrix components from the error matrix may cause a decrease in a distance between the target ECG signal and the reference ECG signal. Due to the decrease, the norm of the error matrix from which the dominant error matrix components are eliminated may be less than the norm of the error matrix including the dominant error matrix components, for example, $L_i < M_i$. Thus, an increase may occur in a difference $|L_i - M_i|$ between the norm of the error matrix from which the dominant error matrix components are eliminated and the norm of the error matrix including the dominant error matrix components. When the user attempting to be authenticated does not match the pre-registered user, the distance between the target ECG signal and the reference ECG signal may not decrease despite the eliminating of the dominant error matrix components such that the norm of the error matrix from which the dominant error matrix components are eliminated may be similar to the norm of the error matrix including the dominant error matrix components. The authenticator 240 may set a predetermined threshold norm. When the norm of the error matrix from which the dominant error matrix components are eliminated is less than or equal to the predetermined threshold norm, the authenticator 240 may authenticate that the target ECG signal corresponds to the reference ECG signal. When the norm is used to determine whether the target ECG signal corresponds to the reference ECG signal, an accuracy in determining whether the user corresponds to the pre-registered user may increase, thereby reducing a false acceptance rate (FAR) and a false rejection rate (FRR) in the authentication apparatus 210.

When a plurality of users is registered in advance, the authenticator 240 may extract a norm for each of a plurality of reference ECG signals indicating ECG signals of the pre-registered users, and determine a pre-registered user having a reference ECG signal corresponding to a smallest norm among a plurality of norms, as a user attempting to be authenticated. For example, when a first user and a second user are registered in advance, and when a third user attempts to be authenticated, the authenticator 240 may generate a first norm by eliminating dominant error components and an average value of an ECG signal of the first user from an ECG signal of the third user, and generate a second norm by eliminating dominant error components and an average value of an ECG signal of the second user from the ECG signal of the third user. In this example, when the first norm and the second norm are less than or equal to the threshold norm, the authenticator 240 may determine the third user matches a pre-registered user corresponding to a smaller norm between the first norm and the second norm. For example, when the first norm is smaller than the second norm, the authenticator 240 may authenticate the third user as matching the first user.

Figure 3:
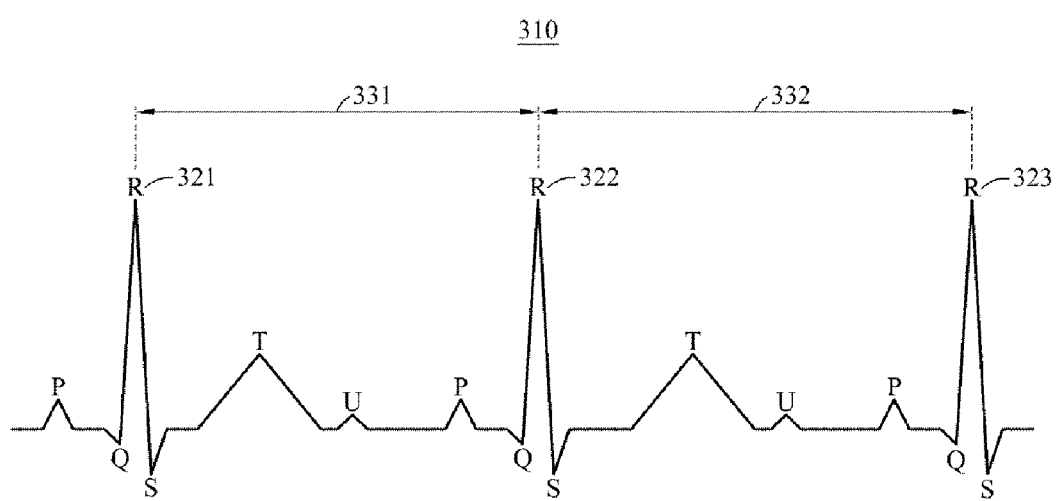
FIG. 3 is a diagram illustrating an example of aligning an electrocardiogram (ECG) signal.

FIG. 3 is a diagram illustrating an example of aligning an ECG signal 310. Referring to FIG. 3, a P wave, a QRS wave, a T wave, and a U wave appear repetitively in the ECG signal 310. An authentication apparatus may align the ECG signal 310 to reduce an FAR and an FRR. In this example, the authentication apparatus may align the ECG signal 310 based on R peaks 321, 322, and 323 of the QRS wave, which are the highest peaks among peaks of the P wave, the QRS wave, the T wave, and the U wave. The authentication apparatus may set each of an interval between the R peaks 321 and 322 and an interval between the R peaks 322 and 323 as a single time period. Thus, the authentication apparatus may extract a first ECG waveform 331 and a second ECG waveform 332 aligned based on the R peaks 321, 322, and 323 from the ECG signal 310, and authenticate whether a user having the ECG signal 310 is a pre-registered user based on the first ECG waveform 331 and the second ECG waveform 332.

Figure 4A:
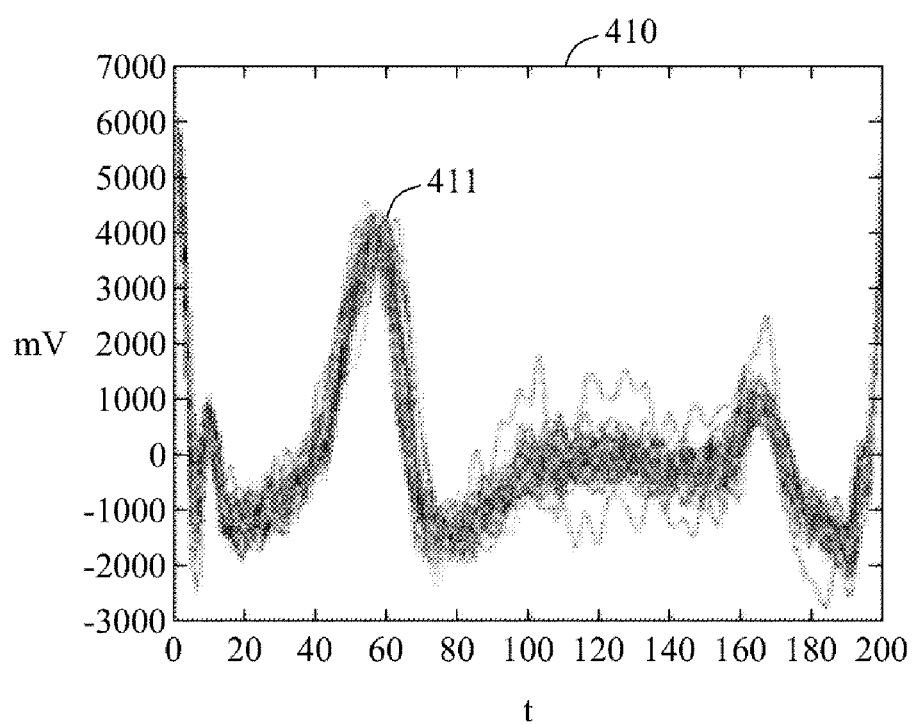
FIGS. 4A and 4B are diagrams illustrating examples of preprocessing an ECG signal.
Figure 4B:
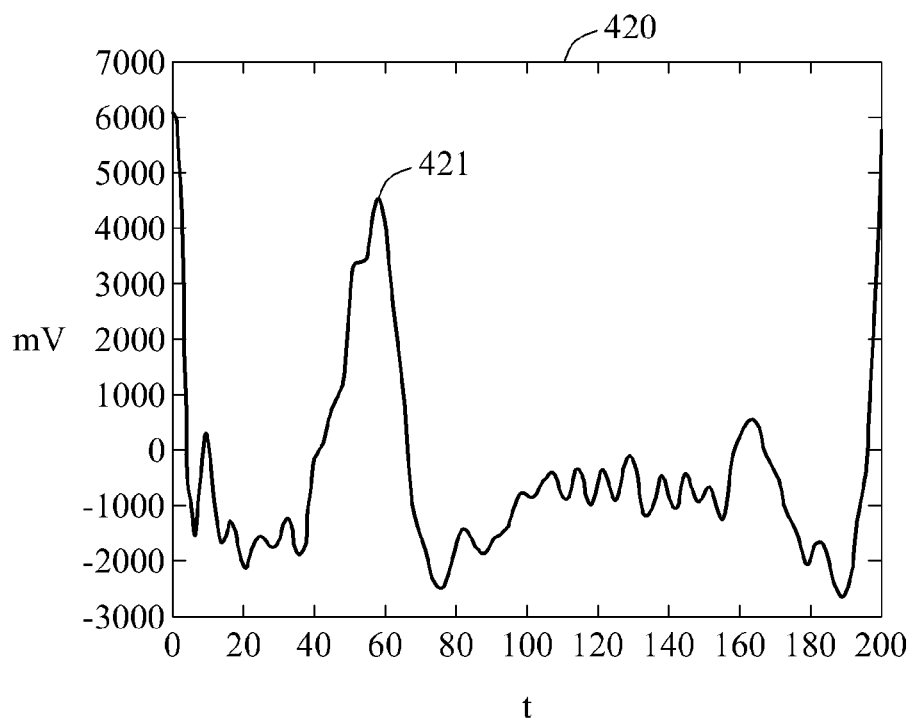

FIGS. 4A and 4B are diagrams illustrating examples of preprocessing an ECG signal 411 or 421. Referring to FIGS. 4A and 4B, horizontal axes represent a time and vertical axes represent a voltage level in graphs 410 and 420. The ECG signal 411 refers to a raw ECG signal sensed in an ECG sensor. An authentication apparatus may align the ECG signal 411 based on an R peak, and set an interval between consecutive R peaks as a single time period, thereby normalizing the ECG signal 411 based on the set time period. In this example, the authentication apparatus may normalize an amplitude of the ECG signal 411 based on a predetermined voltage level, and also normalize the ECG signal 411 based on a predetermined frequency band.

Also, the authentication apparatus may extract the ECG signal 421 by eliminating a component having a relatively low correlation from the ECG signal 411. The authentication apparatus may authenticate a user based on the ECG signal 421 having a less number of components than a number of components included in the ECG signal 411, thereby reducing a number of operations and an amount of time used for the operations.

Figure 5:
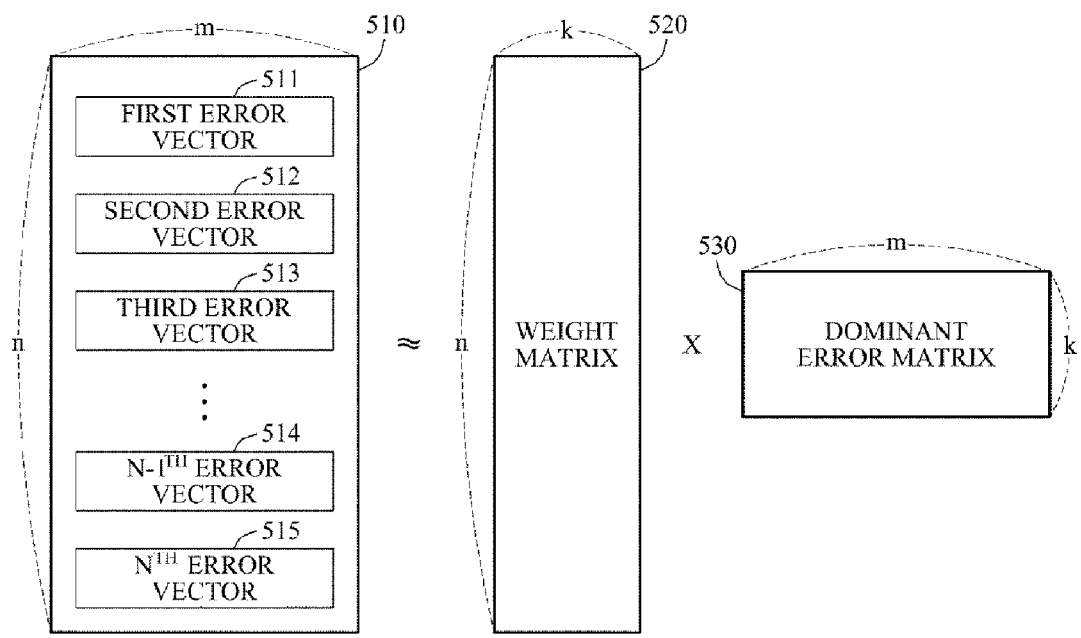
FIG. 5 is a diagram illustrating an example of a dominant error matrix.

FIG. 5 is a diagram illustrating an example of a dominant error matrix 530. Referring to FIG. 5, a registration apparatus acquires an ECG signal from a user attempting to be registered. The ECG signal includes n ECG waveforms, and the registration apparatus generates n ECG vectors based on the n ECG waveforms. The registration apparatus generates an average vector by determining an average of the n ECG vectors. The registration apparatus generates n error vectors, for example, a first error vector 511, a second error vector 512, a third error vector 513, an n−1$^{th}$ error vector 514, and an n$^{th}$ error vector 515, by subtracting the average vector from each of the n ECG vectors, and generates an error matrix 510 based on the n error vectors. In this example, the n ECG vectors have m dimensions, and thus, a size of the error matrix 510 is n×m.

The registration apparatus decomposes the error matrix 510 into a weight matrix 520 and the dominant error matrix 530 based on an SVD scheme. The dominant error matrix 530 represents a pattern based on unique characteristics of the user. In this example, a rank of the dominant error matrix 530 is k, which is lower than n that is a rank of the error matrix 510. The registration apparatus may store extracted information including, for example, the average vector, the error matrix 510, and the dominant error matrix 530, in a memory, and transmit the information to an authentication apparatus through a communication interface.

Figure 6:
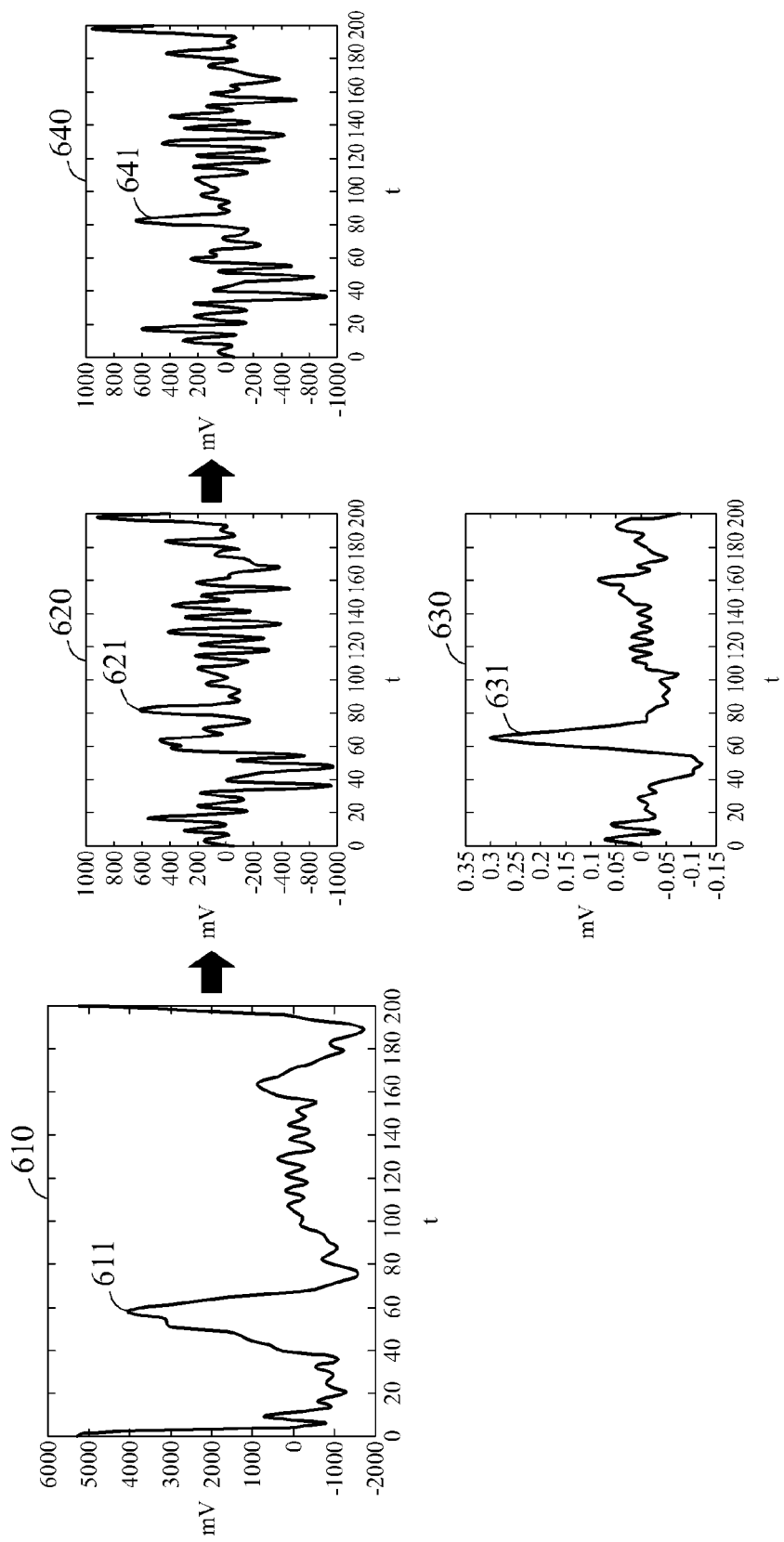
FIG. 6 is a diagram illustrating an example of a user authentication.

FIG. 6 is a diagram illustrating an example of a user authentication. Referring to FIG. 6, horizontal axes represent a time and vertical axes represent a voltage level in graphs 610 through 640. An ECG signal 611 refers to a target ECG signal obtained by filtering a raw target ECG signal acquired from a user. A signal 621 refers to a signal corresponding to an error matrix generated by subtracting an average vector of a plurality of ECG vectors extracted from a plurality of ECG waveforms of the ECG signal 611. The average vector indicates an average value of a reference ECG waveform. A signal 631 refers to a signal corresponding to a dominant error matrix indicating dominant error components of a reference ECG signal. A signal 641 refers to a signal corresponding to an error matrix obtained by eliminating dominant error matrix components from the error matrix of the signal 621.

In FIG. 6, when a norm of the signal 641 is less than or equal to a threshold norm, the user of the ECG signal 611 may match a user of the reference ECG signal. Thus, when the norm of the signal 641 is less than or equal to the threshold norm, the user may be authenticated to be the same as the user registered in an authentication apparatus in advance.

Figure 7:
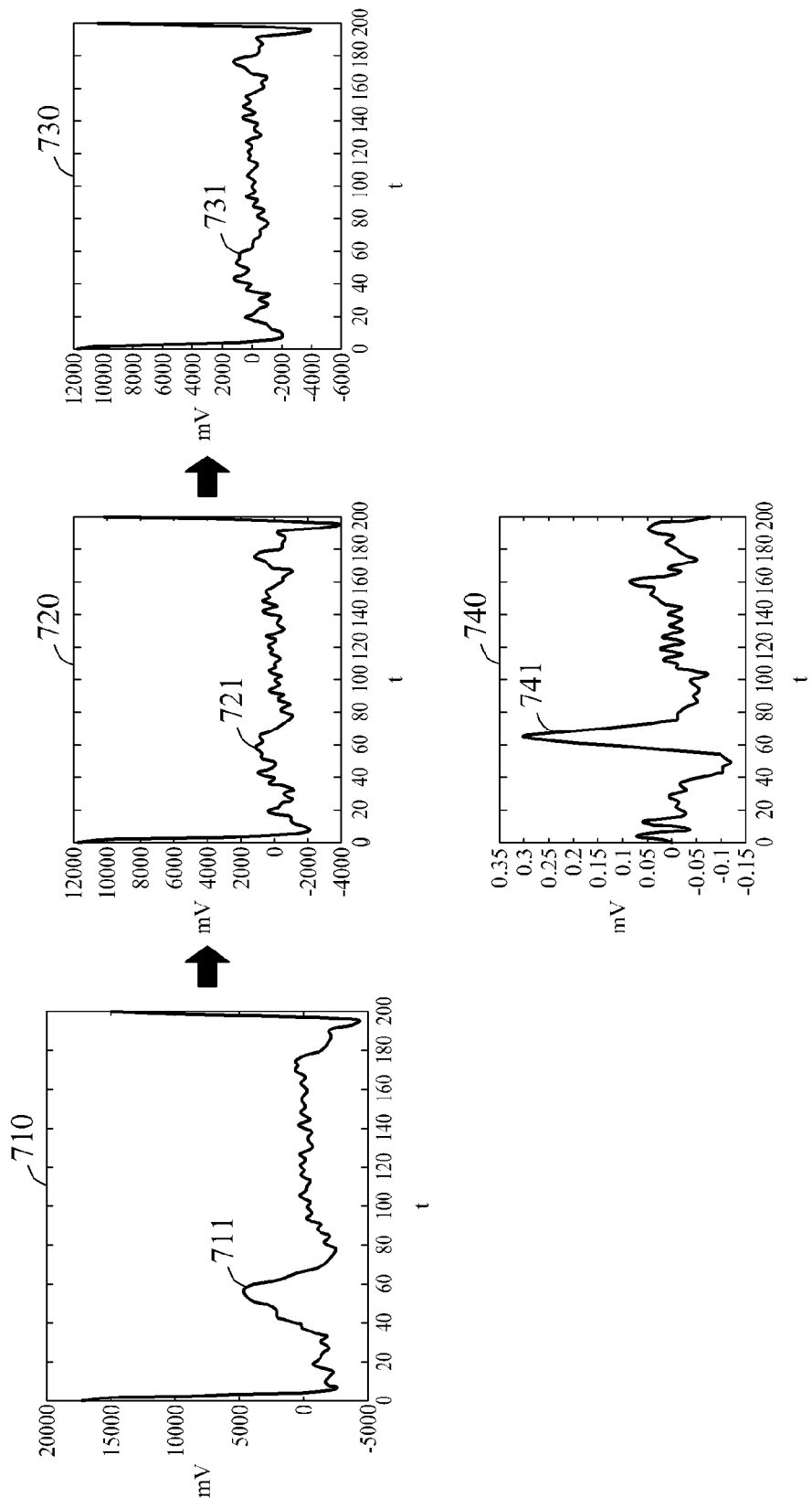
FIG. 7 is a diagram illustrating another example of a user authentication.

FIG. 7 is a diagram illustrating another example of a user authentication. Referring to FIG. 7, horizontal axes represent a time and vertical axes represent a voltage level in graphs 710 through 740. An ECG signal 711 refers to a target ECG signal obtained by filtering a raw target ECG signal acquired form a user. A signal 721 refers to a signal corresponding to an error matrix generated by subtracting an average vector of at least one ECG vector extracted from at least one ECG waveform of the ECG signal 711. The average vector indicates an average value of a plurality of ECG waveforms in a reference ECG signal corresponding to an ECG signal of a pre-registered user. A signal 731 refers to a signal corresponding to a dominant error matrix indicating dominant error components of the reference ECG signal. A signal 741 refers to a signal corresponding to an error matrix obtained by eliminating dominant error matrix components from the error matrix of the signal 721.

In FIG. 7, when a norm of the signal 741 is greater than a threshold norm, the user of the ECG signal 711 may differ from the user of the reference ECG signal. Thus, the user may be authenticated to be different from the user registered in an authentication apparatus in advance.

Figure 8:
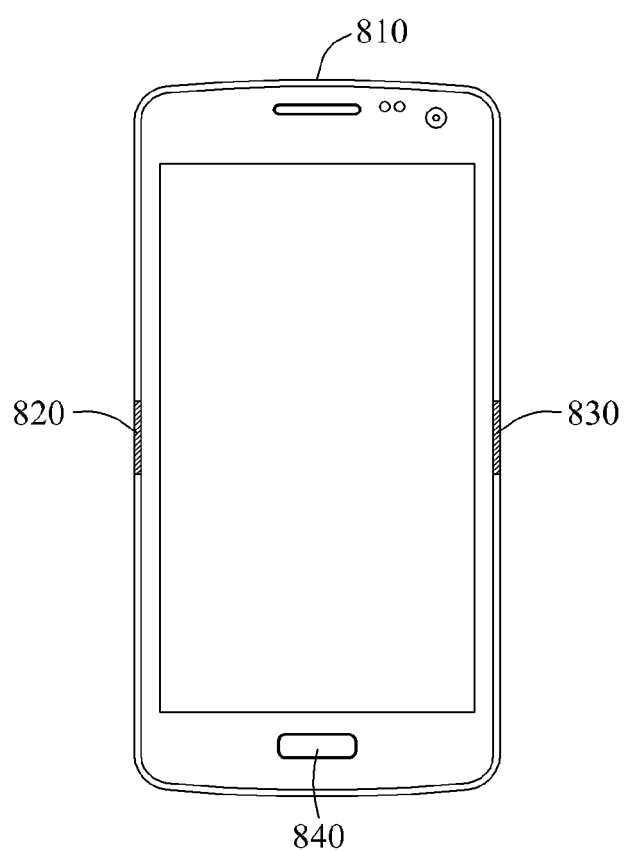
FIG. 8 is a diagram illustrating an example of an authentication apparatus.

FIG. 8 is a diagram illustrating an example of an authentication apparatus. Referring to FIG. 8, a mobile terminal 810 includes a positive pole electrode 820, a reference electrode 830, and a negative pole electrode 840 to sense an ECG signal. In this example, the positive pole electrode 820 and the reference electrode 830 are disposed on both sides of the mobile terminal 810, and the negative pole electrode 840 is disposed on a lower portion of the mobile terminal 810.

When a finger of a user comes into contact with a plurality of electrodes, for example, the positive pole electrode 820, the reference electrode 830, and the negative pole electrode 840, the mobile terminal 810 may sense the ECG signal of the user. The mobile terminal 810 may amplify the ECG signal, using an AFE, and convert the amplified ECG signal into a digital signal.

When the ECG signal of the user is registered, the mobile terminal 810 may align the ECG signal based on an R peak, normalize the ECG signal based on a time period of the ECG signal that is set based on an interval between consecutive R peaks, and eliminate a component having a relatively low correlation, among a plurality of components, from the normalized ECG signal, thereby filtering the ECG signal. Also, the mobile terminal 810 may generate a plurality of ECG vectors based on the ECG signal, and determine an average vector indicating an average of the ECG vectors. The mobile terminal 810 may generate an error matrix by subtracting the average vector from the ECG vectors, and extract a dominant error matrix from the error matrix based on an SVD scheme.

When the user attempts to be authenticated, the mobile terminal 810 may align the ECG signal based on the R peak, normalize the ECG signal based on the time period of the ECG signal that is set based on the interval between the consecutive R peaks, and eliminate a component having a relatively low correlation with a pre-registered reference ECG signal, from the normalized ECG signal, thereby filtering the ECG signal. Also, the mobile terminal may generate the plurality of ECG vectors based on the ECG signal, and generate an error matrix by subtracting an average vector of the reference ECG signal from the ECG vectors. The mobile terminal 810 may eliminate dominant error matrix components indicating dominant error components of the reference ECG signal from the error matrix, and generate a norm of the error matrix from which the dominant error matrix components are eliminated. In this example, the dominant error matrix and the average vector of the reference ECG signal may be stored in a memory of the mobile terminal 810 in advance. Also, information of the dominant error matrix and the average vector of the reference ECG signal may be received from an external source, for example, an authentication apparatus. Based on the determined norm, the mobile terminal 810 may authenticate whether the user having the finger in contact with the plurality of electrodes is a pre-registered user.

Figure 9:
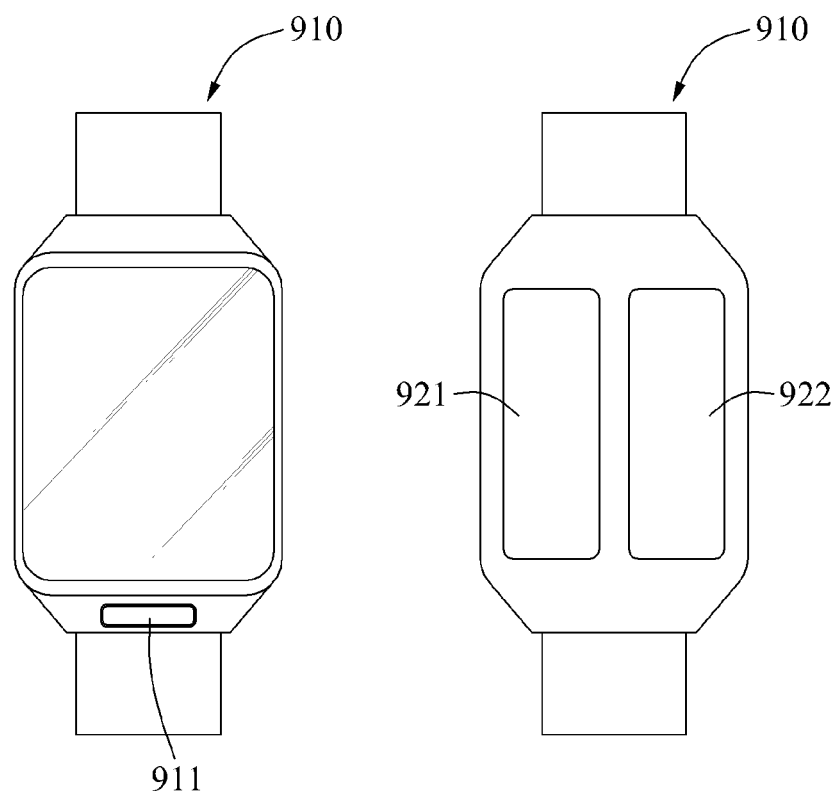
FIG. 9 is a diagram illustrating another example of an authentication apparatus.

FIG. 9 is a diagram illustrating another example of an authentication apparatus. Referring to FIG. 9, a wearable terminal 910 includes a positive pole electrode 921, a reference electrode 922, and a negative pole electrode 911 to sense an ECG signal. In this example, the positive pole electrode 921 and the reference electrode 922 are disposed on a rear side of the wearable terminal 910, and the negative pole electrode 911 is disposed on a front side of the wearable terminal 910.

Similarly to the mobile terminal 810 of FIG. 8, the wearable terminal 910 may acquire the ECG signal of a user using a plurality of electrodes, for example, the positive pole electrode 921, the reference electrode 922, and the negative pole electrode 911, and filter the ECG signal. Also, the wearable terminal 910 may perform an identical operation to the operation of the mobile terminal 810 of the FIG. 8 to register the ECG signal of the user in advance, and authenticate whether the user matches a pre-registered user.

Figure 10:
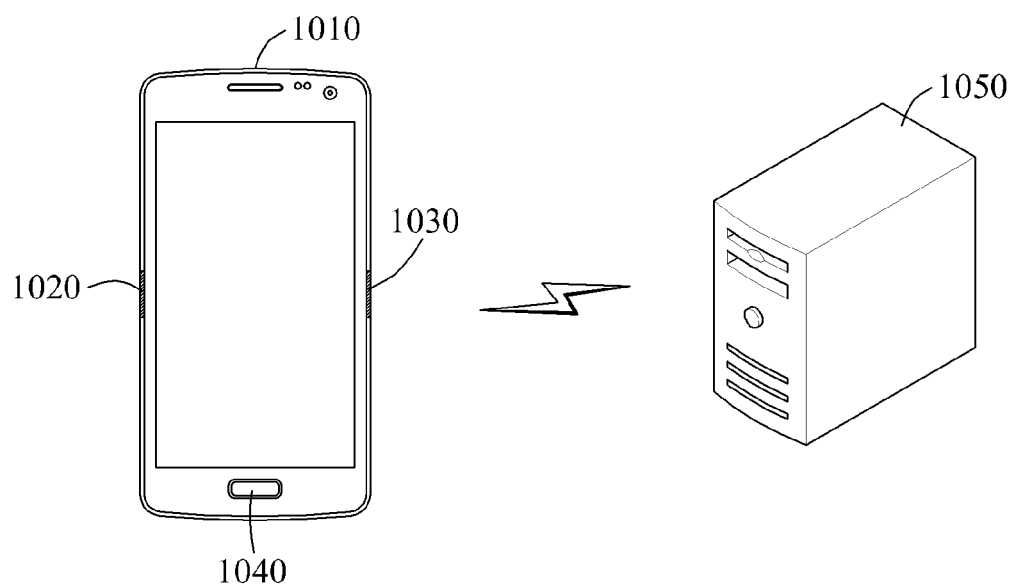
FIG. 10 is a diagram illustrating still another example of an authentication apparatus.

FIG. 10 is a diagram illustrating still another example of an authentication apparatus. Referring to FIG. 10, the mobile terminal 1010 includes a positive pole electrode 1020, a reference electrode 1030, and a negative pole electrode 1040 to sense an ECG signal Similarly to the mobile terminal 810 of FIG. 8, the mobile terminal 1010 may align an ECG signal of a user based on an R peak, and normalize the ECG signal based on a time period of the ECG signal that is set based on an interval between consecutive R peaks. Also, the mobile terminal 1010 may receive information of a reference ECG signal indicating a pre-registered ECG signal from a server 1050, and eliminate a component having a relatively low correlation with the reference ECG signal from the normalized ECG signal, thereby filtering the ECG signal. Also, the mobile terminal 1010 may generate a plurality of ECG vectors based on the ECG signal, and receive information of a dominant error matrix indicating dominant error components of the reference ECG signal and an average vector of the reference ECG signal from the server 1050. The mobile terminal 1010 may generate an error matrix by subtracting the average vector of the reference ECG signal from the ECG vectors. The mobile terminal 1010 may eliminate dominant error matrix components of the reference ECG signal from the error matrix, and determine a norm of the error matrix from which the dominant error matrix components are eliminated. Based on the determined norm, the mobile terminal 1010 may authenticate whether the user having a finger in contact with the plurality of electrodes is a pre-registered user. Also, the mobile terminal 1010 may transmit at least one of information of the error matrix, information of the error matrix from which the dominant error matrix components are eliminated, and authentication information of whether the user matches the pre-registered user to the server 1050. The server 1050 may allow the user to access the server 1050 based on the authentication information received from the mobile terminal 1010.

Figure 11:
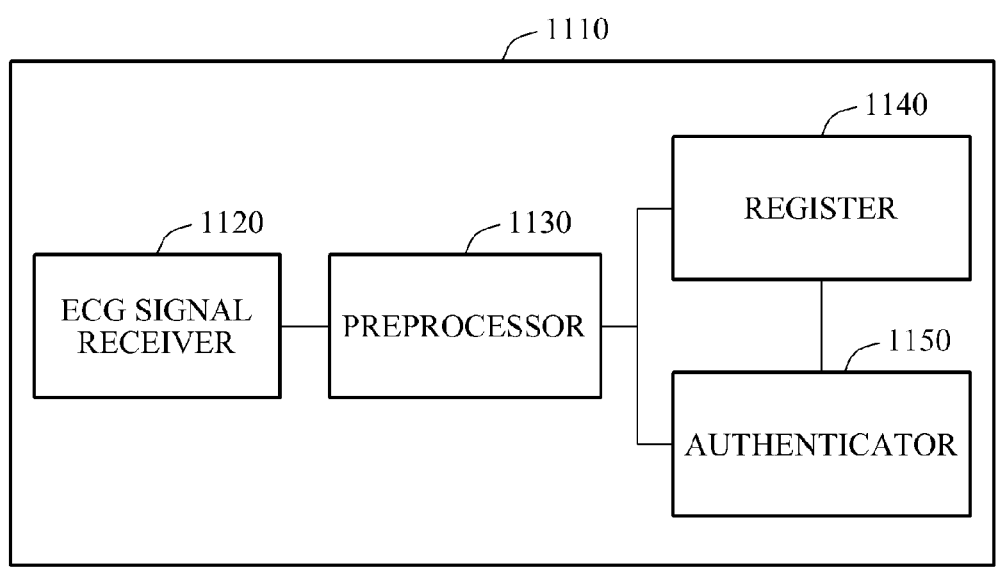
FIG. 11 is a block diagram illustrating another example of an authentication apparatus.

FIG. 11 is a block diagram illustrating another example of an authentication apparatus 1110. Referring to FIG. 11, the authentication apparatus 1110 includes the ECG signal receiver 1120, the preprocessor 1130, a register 1140, and an authenticator 1150.

The ECG signal receiver 1120 receives a first ECG signal and a second ECG signal.

The preprocessor 1130 filters the first ECG signal of a user to be registered, and the second ECG signal of a user to be authenticated. In this example, although not shown in FIG. 11, the preprocessor 1130 may include an aligner configured to align the first ECG signal and the second ECG signal based on an R peak, a normalizer configured to normalize the first ECG signal and the second ECG signal based on time periods of the first ECG signal and the second ECG signal, each time period corresponding to an interval between consecutive R peaks, and an eliminator configured to eliminate a component having a relatively low correlation with the normalized first ECG signal among a plurality of components from the normalized second ECG signal.

The register 1140 extracts a unique pattern from the filtered first ECG signal including dominant error components, and registers information of the user associated with the first ECG signal. In an example, the register 1140 may extract a plurality of first ECG vectors based on a plurality of ECG waveforms of the filtered first ECG signal, and extract an average vector indicating an average value of the filtered first ECG signal by determining an average of the first ECG vectors. Also, the register 1140 may extract a first error matrix based on a difference between the average vector and each of the first ECG vectors, and extract a dominant error matrix indicating dominant error components from the first error matrix based on an SVD scheme.

The authenticator 1150 processes the filtered second ECG signal based on the unique pattern of the filtered first ECG signal, and determines whether the second ECG signal corresponds to the first ECG signal. In an example, the authenticator 150 may extract a plurality of second ECG vectors based on a plurality of second ECG waveforms of the filtered second ECG signal, extract a second error matrix based on a difference between an average vector and each of the second ECG vectors, and determine whether the second ECG signal corresponds to the first ECG signal by eliminating dominant error matrix components from the second error matrix. Also, the authenticator 1150 may determine a norm of the second error matrix from which the dominant error matrix components are eliminated, and determine whether the second ECG signal corresponds to the first ECG signal based on the determined norm.

Repeated descriptions with respect to the authentication apparatus 1110 of FIG. 11 will be omitted for increased clarity and conciseness because the descriptions provided with reference to FIGS. 1 through 10 are also applicable to the authentication apparatus 1110 of FIG. 11.

Figure 12:
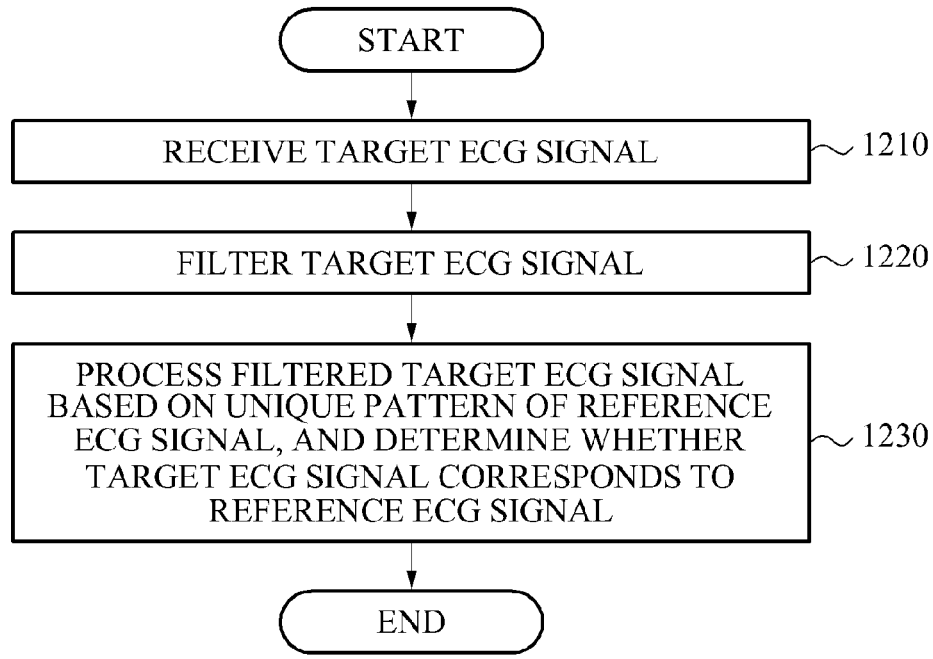
FIG. 12 is a flowchart illustrating an example of an authentication method.

FIG. 12 is a flowchart illustrating an example of an authentication method. Referring to FIG. 12, in operation 1210, an authentication apparatus receives a target ECG signal.

In operation 1220, the authentication apparatus filters the target ECG signal.

In operation 1230, the authentication apparatus processes the filtered target ECG signal based on a unique pattern of a reference ECG signal, and determines whether the target ECG signal corresponds to the reference ECG signal based on the processing.

Repeated descriptions with respect to the authentication method of FIG. 12 will be omitted for increased clarity and conciseness because the descriptions provided with reference to FIGS. 1 through 11 are also applicable to the authentication method of FIG. 12.

Figure 13:
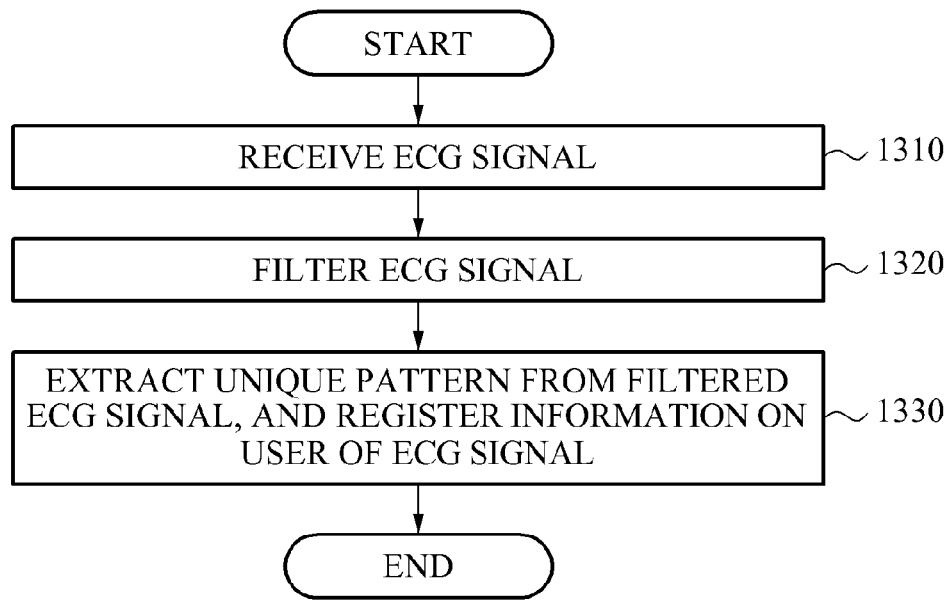
FIG. 13 is a flowchart illustrating an example of a registration method.

FIG. 13 is a flowchart illustrating an example of a registration method. Referring to FIG. 13, in operation 1310, a registration apparatus receives an ECG signal.

In operation 1320, the registration apparatus filters the ECG signal.

In operation 1330, the registration apparatus extracts a unique pattern from the filtered ECG signal including dominant error components, and registers information on a user of the ECG signal.

Repeated descriptions with respect to the registration method of FIG. 13 will be omitted for increased clarity and conciseness because the descriptions provided with reference to FIGS. 1 through 11 are also applicable to the registration method of FIG. 13.

Figure 14:
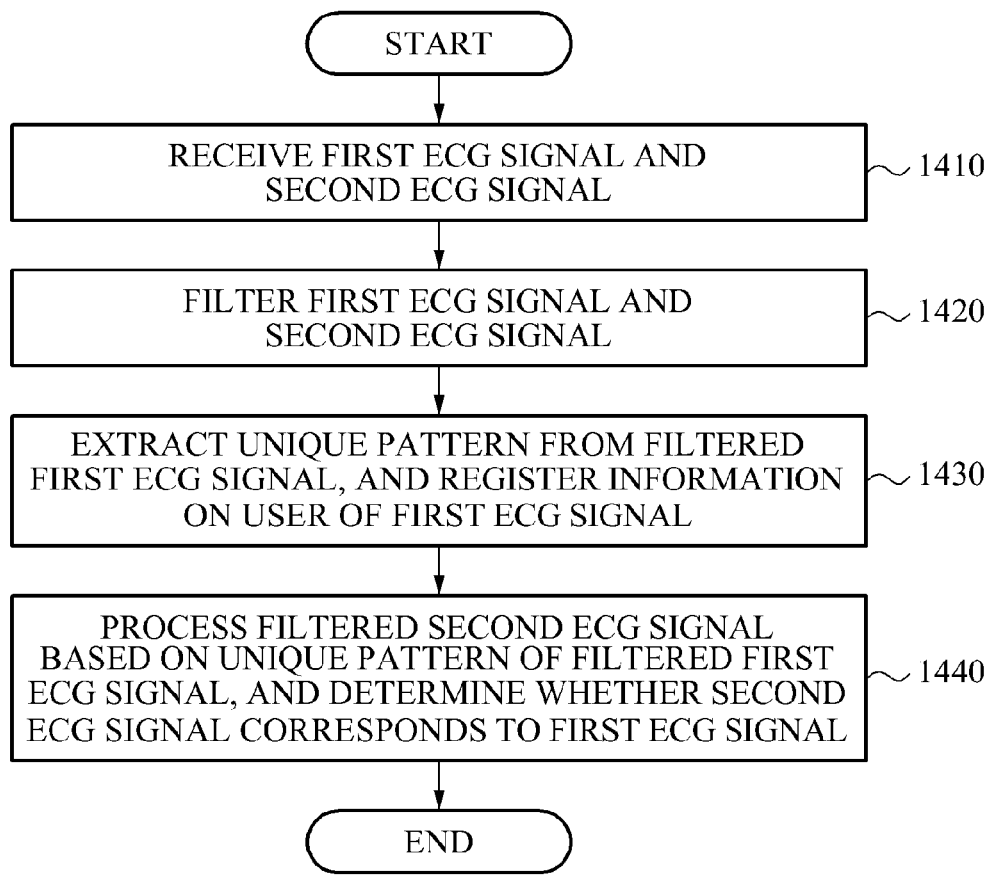
FIG. 14 is a flowchart illustrating another example of an authentication method.

FIG. 14 is a flowchart illustrating another example of an authentication method. Referring to FIG. 14, in operation 1410, an authentication apparatus receives a first ECG signal and a second ECG signal.

In operation 1420, the authentication apparatus filters the first ECG signal and the second ECG signal.

In operation 1430, the authentication apparatus extracts a unique pattern from the filtered first ECG signal including dominant error components, and registers information on a user of the first ECG signal.

In operation 1440, the authentication apparatus processes the filtered second ECG signal based on the unique pattern of the filtered first ECG signal, and determines whether the second ECG signal corresponds to the first ECG signal based on the processing.

Repeated descriptions with respect to the authentication method of FIG. 14 will be omitted for increased clarity and conciseness because the descriptions provided with reference to FIGS. 1 through 11 are also applicable to the authentication method of FIG. 14.

The various elements and methods described above may be implemented using one or more hardware components, or a combination of one or more hardware components and one or more software components.

A hardware component may be, for example, a physical device that physically performs one or more operations, but is not limited thereto. Examples of hardware components include microphones, amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

As a non-exhaustive illustration only, a terminal or apparatus described herein may refer to mobile devices such as, for example, a cellular phone, a smart phone, a wearable smart device (such as, for example, a ring, a watch, a pair of glasses, a bracelet, an ankle bracket, a belt, a necklace, an earring, a headband, a helmet, a device embedded in the cloths or the like), a personal computer (PC), a tablet personal computer (tablet), a phablet, a personal digital assistant (PDA), a digital camera, a portable game console, an MP3 player, a portable/personal multimedia player (PMP), a handheld e-book, an ultra mobile personal computer (UMPC), a portable lab-top PC, a global positioning system (GPS) navigation, and devices such as a high definition television (HDTV), an optical disc player, a DVD player, a Blue-ray player, a setup box, or any other device capable of wireless communication or network communication consistent with that disclosed herein. In a non-exhaustive example, the wearable device may be self-mountable on the body of the user, such as, for example, the glasses or the bracelet. In another non-exhaustive example, the wearable device may be mounted on the body of the user through an attaching device, such as, for example, attaching a smart phone or a tablet to the arm of a user using an armband, or hanging the wearable device around the neck of a user using a lanyard.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An authentication apparatus comprising:
   an electrocardiogram (ECG) signal receiver configured to receive a target ECG signal;
   a preprocessor configured to filter the target ECG signal; and
   an authenticator configured to:
   determine a difference between the filtered target ECG signal and a reference ECG signal;
   eliminate, from the difference, a pattern of the reference ECG signal; and
   determine whether the target ECG signal corresponds to the reference ECG signal based on the eliminating.

2. The apparatus of claim 1, wherein the preprocessor is further configured to:
   align the target ECG signal based on an R peak of the target ECG signal; and
   normalize the target ECG signal based on a time interval between consecutive R peaks of the target ECG signal.

3. The apparatus of claim 2, wherein the preprocessor is further configured to:
   normalize an amplitude of the target ECG signal based on a predetermined voltage level.

4. The apparatus of claim 1, wherein the authenticator is further configured to:
   extract an ECG vector based on an ECG waveform of the filtered target ECG signal; and
   extract an error matrix indicating the difference between the filtered target ECG signal and the reference ECG signal based on a difference between an average vector indicating an average of ECG waveforms of the reference ECG signal and the ECG vector.

5. The apparatus of claim 4, wherein the authenticator is further configured to:
eliminate, from the error matrix, dominant error matrix components of the reference ECG signal, the dominant error matrix components indicating the pattern.

6. The apparatus of claim 5, wherein the authenticator is further configured to:
determine a norm of the error matrix from which the dominant error matrix components are eliminated; and
determine whether the target ECG signal corresponds to the reference ECG signal based on the norm.

7. The apparatus of claim 6, wherein the authenticator is further configured to:
authenticate the target ECG signal as corresponding to the reference ECG signal in response to the norm being less than or equal to a predetermined norm.

8. The apparatus of claim 6, wherein, in response to reference ECG signals being acquired, the authenticator is further configured to:
extract the norm for each of the reference ECG signals; and
authenticate a reference ECG signal having a smallest norm among the reference ECG signals as corresponding to the target ECG signal.

9. A registration apparatus comprising:
an electrocardiogram (ECG) signal receiver configured to receive an ECG signal;
a preprocessor configured to filter the ECG signal; and
a register configured to
extract a pattern of the filtered ECG signal, and register and store information of the ECG signal, the information comprising the pattern,
extract ECG vectors based on ECG waveforms of the filtered ECG signal;
determine an average of the ECG vectors to extract an average vector indicating an average of the filtered ECG signal by determining an average of the ECG vectors;
determine a difference between the average vector and each of the ECG vectors to extract an error matrix; and
extract a dominant error matrix indicating dominant error components from the error matrix based on a singular value decomposition (SVD) scheme.

10. The apparatus of claim 9, wherein the preprocessor is further configured to:
align the ECG signal based on an R peak of the ECG signal; and
normalize the ECG signal based on a time interval between consecutive R peaks of the ECG signal.

11. The apparatus of claim 9, wherein the register is further configured to:
determine a difference between the filtered ECG signal and an average of the filtered ECG signal.

12. The apparatus of claim 9, wherein a rank of the dominant error matrix is lower than a rank of the error matrix.

13. An authentication apparatus comprising:
an electrocardiogram (ECG) signal receiver configured to receive a first ECG signal and a second ECG signal;
a preprocessor configured to filter the first ECG signal and the second ECG signal;
a register configured to extract a pattern from the filtered first ECG signal, and register information of the first ECG signal, the information comprising the pattern; and
an authenticator configured to process the filtered second ECG signal based on the pattern of the filtered first ECG signal, and determine whether the second ECG signal corresponds to the first ECG signal based on the processing.

14. The apparatus of claim 13, wherein the preprocessor is further configured to:
align the first ECG signal and the second ECG signal based on an R peak of the first ECG signal and an R peak of the second ECG signal; and
normalize the first ECG signal and second ECG signal based on time intervals between consecutive R peaks of the first ECG signal and time intervals between consecutive R peaks of the second ECG signal.

15. The apparatus of claim 13, wherein the register is further configured to:
extract first ECG vectors based on ECG waveforms of the filtered first ECG signal; and
extract an average vector indicating an average of the filtered first ECG signal by determining an average of the first ECG vectors.

16. The apparatus of claim 15, wherein the register is further configured to:
extract a first error matrix based on a difference between the average vector and each of the first ECG vectors; and
extract a dominant error matrix indicating dominant error components from the first error matrix based on a singular value decomposition (SVD) scheme.

17. The apparatus of claim 16, wherein the authenticator is further configured to:
extract a second ECG vector based on a second ECG waveform of the filtered second ECG signal;
extract a second error matrix indicating a difference between the filtered second ECG signal and the filtered first ECG signal based on a difference between the average vector and the second ECG vector; and
eliminate, from the second error matrix, dominant error matrix components of the filtered first ECG signal, the dominant error matrix components indicating the pattern.

18. The apparatus of claim 17, wherein the authenticator is further configured to:
determine a norm of the second error matrix from which the dominant error matrix components are eliminated; and
determine whether the second ECG signal corresponds to the first ECG signal based on the norm.

19. A method comprising:
filtering a first ECG signal; and
determining a difference between the filtered first ECG signal and the second ECG signal;
eliminating, from the difference, a pattern of the second ECG signal; and
determining whether the first ECG signal corresponds to the second ECG signal based on the difference from which the pattern of the second ECG signal is eliminated.

20. The method of claim 19, further comprising:
filtering the second ECG signal;
extracting the pattern from the filtered second ECG signal; and
registering the extracted pattern of the second ECG signal.

21. The method of claim 20, wherein the extracting comprises:
determining a difference between the filtered second ECG signal and an average of the filtered second ECG signal; and extracting, from the difference, the pattern of the filtered second ECG signal.

* * * * *